United States Patent [19]

Lines

[11] 4,144,132

[45] Mar. 13, 1979

[54] PRODUCTION OF SINGLE-CELL PROTEIN FROM POTATO PROCESSING WASTE

[76] Inventor: Kent K. Lines, 3500 Blysworth Ct., Apt. N, Winston-Salem, N.C. 27106

[21] Appl. No.: 823,673

[22] Filed: Aug. 11, 1977

[51] Int. Cl.$^2$ ................... 426 53; A23J 1/16; A23J 1/18

[52] U.S. Cl. ................... 195/82; 195/28 R; 195/83; 195/88; 195/111; 426/52

[58] Field of Search ............ 195/27, 28 R, 82, 83, 195/111, 88, 90; 426/52, 53

[56] References Cited

U.S. PATENT DOCUMENTS

| | | | |
|---|---|---|---|
| 3,105,799 | 10/1963 | Tveit | 195/82 |
| 4,018,650 | 4/1977 | Busta et al. | 195/28 R |
| 4,046,789 | 9/1977 | Muller et al. | 195/27 |

OTHER PUBLICATIONS

Food Engineering, Nov. 1976, pp. 66–67.

*Primary Examiner*—Lionel M. Shapiro
*Attorney, Agent, or Firm*—Christie, Parker & Hale

[57] ABSTRACT

A semi-solid filter cake waste product from potato processing is used as a growth medium for producing single-cell protein. A pre-fermenting yeast, such as *Endomycopsis fibuliger*, is introduced into the growth medium to produce amylase for breaking down into glucose the starch naturally present in the potato waste medium. A primary fermenting yeast, such as *Candida utilis*, is introduced to the potato waste medium and uses the glucose for growth.

13 Claims, 8 Drawing Figures

GROWTH OF CANDIDA UTILIS ON SABOURAUD LIQUID MEDIUM

GROWTH OF *ENDOMYCOPSIS FIBULIGER* ON SABOURAUD LIQUID MEDIUM

GROWTH OF CANDIDA UTILIS ON POTATO WASTE

Growth of *Candida utilis* on potato waste with 0.2% $(NH_4)_2SO_4$

GROWTH OF CANDIDA UTILIS ON POTATO WASTE WITH 0.15% $KH_2PO_4$

GROWTH OF CANDIDA UTILIS ON 7% GLUCOSE MINIMAL MEDIUM

GROWTH OF CANDIDA UTILIS ON 0.1% GLUCOSE MINIMAL MEDIUM

PRODUCTION OF SINGLE-CELL PROTEIN FROM POTATO PROCESSING WASTE

BACKGROUND

This invention relates to production of single-cell protein from potato processing waste.

Production of yeast as a primary food source may provide a partial solution to the world food problem. Yeasts have been recognized as dependable food sources for many years. They are very good sources of protein, being comparable to meat and soybean. They also supply amino acids in quantities that make them as good a source as soybean, milk, egg and meat. In addition, they are valuable sources of the B-vitamins. Yeasts are therefore prime candidates to help eradicate protein deficiencies and the vitamin deficiency diseases such as beriberi and pellagra.

*Saccharomyces cerevisiae* and *Candida utilis* have been commonly used as food yeasts. As to gross composition, *Saccharomyces cerevisiae* grown on molasses contains 52.4% protein, 37.1% carbohydrates, 1.7% fat, and 8.8% ash. Its elemental composition is 45% carbon, 32% oxygen, 9% nitrogen, 6% hydrogen, and 8% inorganic matter. *Candida utilis* grown on sulfite liquor contains 5.8% moisture, 8% nitrogen, of which nucleic acid nitrogen is 0.4%, 29.6% polysaccharide, 4.8% fat, 0.8% fiber, and 9.0% ash. Thiamine is present as 5 $\mu g/g$ dried cell material, riboflavin as 45 $\mu g/g$, niacin as 415 $\mu g/g$, and pyridoxine as 29 $\mu g/g$. Using the common factor total N × 6.25, about one-half of the dry weight of yeast cells is crude protein. The content of carbohydrates, fats, and proteins in yeasts varies according to growth conditions and substrate employed. Generally, yeasts are used to supplement cereals, to flavor foods, and to add a nutritional supplement to prepared foods.

Food yeasts are grown for human consumption, while fodder yeasts are grown for animal consumption. Usually food yeasts are non-fermenting stable whole yeast cells, carefully prepared and dehydrated to yield flakes or powders intended for improving the human diet. Food yeasts differ from fodder yeasts mainly in quality characteristics. Food yeasts must exhibit lower bacterial and mold contents, higher levels of vitamins, higher protein content, bland flavor, light color, and absence of pathogenic microorganisms. They also must not contain added ingredients or fillers.

Today cultivation of microorganisms for food, since 1966 called single-cell protein (SCP), has become a fairly vigorous field. Yeasts and bacteria have been grown on hydrocarbons, cellulose accumulation, and even on livestock wastes. More traditional methods include use of molasses, sulfite liquor, and whey as growth media.

According to the World Survey of Fermentation Industries, 1963, dried yeast is produced in twenty countries, with a total annual production estimated at 180,000 metric tons dry weight. Of this total, 60% is produced in eastern Europe and the U.S.S.R. as fodder yeast, with molasses and spent sulfite liquor as principal carbon sources. North America produces approximately 37,000 metric tons of dried yeast annually.

Some work has been done using potatoes and potato processing waste water as growth media for various species of yeast. The yeast is grown principally as fodder yeast for feeding cattle and pigs. Since potatoes have a protein-carbohydrate ratio of 1:10 or 1:12, they tend to cause over-fattening of meat carcasses with a resultant loss of muscle mass if they are unfortified when fed to meat animals. The gross composition of potatoes is water 77.9%, protein 2.0%, fat 0.1%, ash 1.0%, and total carbohydrate 19.1%. Fiber makes up 0.4% of the total mass of a potato, with free sugars making up 0.8% and starch making up 14.7%. Vitamins contained in 100 g of raw potato are niacin 1.5 mg, thiamine 100 $\mu g$, riboflavin 40 $\mu g$, vitamin A a trace, and vitamin C 17 mg. The quantity of essential amino acids averages around 100 mg of each per 100 g of raw potato.

Working in Poland, Janicki et al. found that they achieved best yeast growth using 18-20% w/v mixtures of dried, saccharified potato in water. They added nitrogen and phosphate salts and grew *Candida utilis* in aerated tanks at 30°-32° C. Continuous growth with temperature and pH control gave best results, with a yield in the range of 450-530 g of yeast cells per kg of sugar present in the potato medium.

Researchers in Sweden were able to cultivate *Candida utilis* on waste water from potato processing plants. The waste water contained 1.5-4.0% solids, primarily potato starch, and was sterilized before use. *Endomycopsis fibuliger*, a yeast that produces external amylases, was used to break down the starch in the waste water into glucose, which is utilized more rapidly by *C. utilis*. The yeast yield was 45 mg of cells per 100 mg of starch supplied in the waste water. See, for example, *Food Engineering*, Nov. 1976, pp. 66-67.

Reiser, at the University of Idaho, successfully cultivated *Candida utilis* on the waste water from potato starch plants in 1954. The waste water contained 1.2% solids, of which 37% was protein, 12% was sugar, and 0.8% was starch. It was not sterilized before use and no additional growth factors were needed. The yeast was grown in a 30 liter laboratory fermentor at 30°-32° C., at a pH of 5, which is not the optimal pH for the yeast, but which does reduce growth of bacterial contaminants. The yeast yield was about 40% of the solids supplied in the waste water.

The present invention is based on a recognition that very dense potato waste filter cake from potato processing plants can be used as a substrate for the growth of *Candida utilis*. Currently this untreated filter cake is being fed to cattle. The growth of yeast on the filter cake can increase protein content to an extent that it would be a more complete diet for animals.

SUMMARY OF THE INVENTION

Briefly, one practice of the present invention provides a method for producing a single-cell protein by introducing a pre-fermenting yeast into a growth medium comprising a water suspension of particulate raw potato solids, such as the filter cake obtained from potato processing waste. The pre-fermenting yeast breaks down starch in the growth medium into glucose. A primary fermenting yeast is introduced into the growth medium and uses such glucose for its own growth. The primary fermenting yeast also can be grown in the absence of the pre-fermenting yeast, but the growth rate is lower.

In one form of the invention, the growth medium is pre-digested by the pre-fermenting yeast to initiate the process of breaking down the starch into glucose, after which the primary fermenting yeast is introduced into the pre-digested growth medium. In another form of the invention, the pre-fermenting yeast and the primary fermenting yeast can be introduced into the growth medium at substantially the same time. In this instance the starch is pre-digested before the primary fermenting yeast uses it.

Successful results have been produced using *Candida utilis* as the primary fermenting yeast and *Endomycopsis fibuliger* as the pre-fermenting yeast.

DRAWINGS

DETAILED DESCRIPTION

Figure 1:
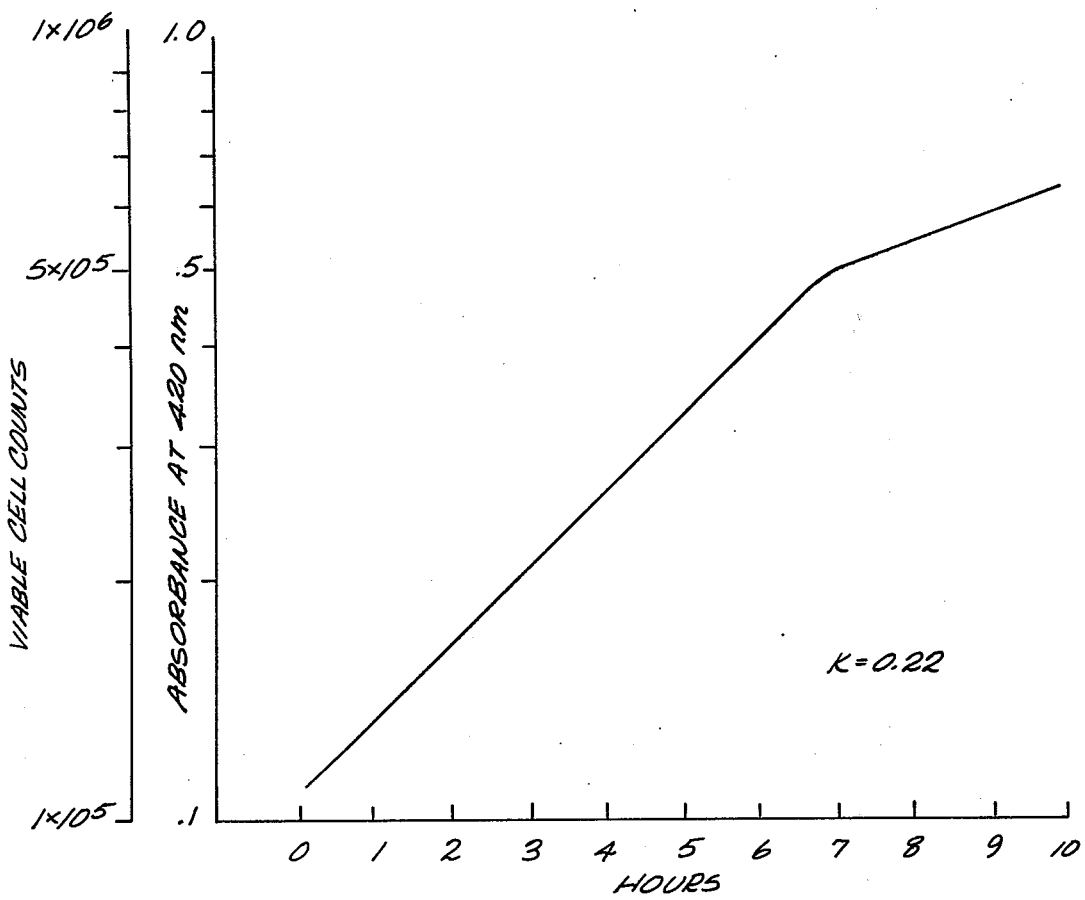
FIG. 1 is a graph illustrating the growth of *Candida utilis* on Sabouraud liquid medium.

According to the present invention, the "filter cake" of potato processing is used as a growth medium for yeast which, in turn, provides a source of single-cell protein to be used for food or feed. The filter cake comprises a water solution of particulate raw potato solids. Such potato solids comprise whole raw potatoes which have been peeled, shredded, sliced, diced, comminuted, or otherwise separated into smaller pieces or particles and eventually collected as a mass of solids in a screening process. This mass of potato solids is typically scraped off the screens and disposed of as a waste product in conventional potato processing operations.

The potato waste is a semi-solid gel-like mass of intact raw, whole potato material and skins suspended in water. Such a mass of potato solids comprises the entire constituents of a whole raw potato, and is to be distinguished from the wash water effluent from potato processing plants which contains dissolved and/or suspended starch. Such starchy waste water includes, for the most part, only a component of a raw whole potato, namely, potato starch, and is a dilute suspension in which the starch is present in the wash water in an amount of about 3% by weight.

According to this invention, an edible pre-fermenting yeast capable of producing external enzymes, such as amylases, is used to aid in breaking down into glucose the starch present in potato waste filter cake. Such a pre-fermenting yeast can be *Endomycopsis fibuliger* ATCC 9947 (NRRL Y-1062). An edible primary fermenting yeast also is used. Such a primary fermenting yeast is one which is capable of utilizing the glucose in the starchy waste material to support its growth. *Candida utilis*, ATCC 9950 (NRRL Y-900), is a primary fermenting yeast which was successfully grown in a growth medium comprised of potato waste material in accordance with principles of this invention.

The present invention is described in the context of growth studies using *Candida utilis* and *Endomycopsis fibuliger* as the primary fermenting yeast and pre-fermenting yeast, respectively. The growth studies were carried out using potato waste filter cake as a substrate. The description to follow shows that these growth studies included: (1) determination of the growth rate of *C. utilis* in laboratory medium, (2) determination of growth rate and yield of *C. utilis* on potato waste medium, with and without added nutrients, and (3) determination of growth rate and yield of *C. utilis* in mixed culture with *E. fibuliger* on potato waste medium. Results of these studies demonstrated that potato waste filter cake is a good substrate for growth of *C. utilis* with the fastest growth rate and highest yield occurring in the mixed culture. Other studies quantitated the amounts of carbohydrate, nitrogen, and phosphorus in potato waste, as well as the amounts of amino acids in potato waste and potato waste plus yeast cells grown on it. Results of these studies showed that potato waste possesses sufficient quantities of these growth factors to support the growth of *C. utilis* and that the presence of yeast increases the amounts of amino acids in potato waste while reducing the amount of carbohydrate.

*Candida utilis* was grown in Sabouraud liquid medium (described below) in order to determine its growth rate in laboratory medium. The purpose was to compare standard growth rates in laboratory media to the growth rates of *C. utilis* in subsequent growth studies carried out on various potato waste media. Sabouraud liquid medium was chosen for standard cultivation of the yeast because the Difco manual recommends it as a good liquid medium for the cultivation of yeasts, molds, and aciduric and acidolophillic bacteria. The acid reaction of the final medium, pH 5.7, was particularly well suited for the cultivation of yeasts and fungi. FIG. 1 illustrates the growth of *C. utilis* in Sabouraud liquid medium at 25° C. in a New Brunswick gyrotory water bath shaker at 100 rotations per minute. Growth was measured turbidimetrically in a Beckman spectrophotometer model 44 at 420 nm and was also measured using counts of viable cells. Average doubling time of the yeast in these conditions was 3.2 hours.

Figure 2:
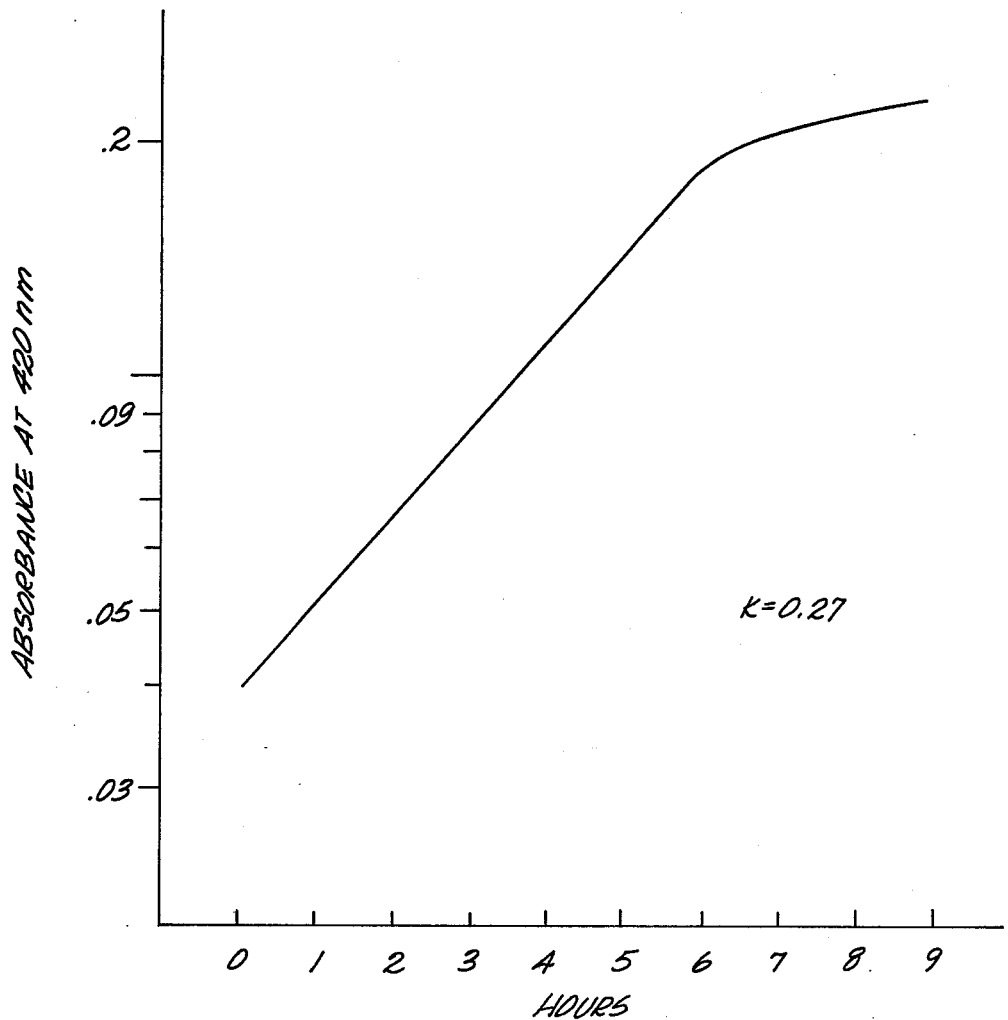
FIG. 2 is a graph illustrating the growth of *Endomycopsis fibuliger* on Sabouraud liquid medium.

*Endomycopsis fibuliger* was also grown on Sabouraud liquid medium in order to establish its growth rate in laboratory medium. Gram stains of the organism at various times during the course of the experiment reveal that it forms pseudomycelia. Daughter cells fail to complete the budding process and remain attached to the mother cell, unlike *C. utilis* which grows as single cells that complete the separation of daughter from mother cell. The pseudomycelia appear to increase their length and branching during exponential growth, which causes sedimentation after about 6 hours. The formation of the pseudomycelia makes it difficult to obtain an accurate growth curve turbidimetrically after that time. However, it was possible to obtain fairly accurate turbidity readings up to the time when the pseudomycelia become so large as to settle rapidly from suspension. FIG. 2 records the growth of *E. fibuliger* in Sabouraud liquid medium at 25° C. in the gyrotory shaker at 100 rotations per minute. Growth was measured tubidimetrically in the Beckman spectrophotometer at 420 mm. The average doubling time of the yeast in these conditions was 2.6 hours. Both yeasts reach their stationary phase after about 7 hours of growth.

A major factor in developing a method of production of a single-cell protein is to determine the conditions of growth that will give the highest yield and fastest growth rate of the organism being cultivated. All substrates must contain certain nutrients if they are to support growth of microorganisms. First, a carbon source must be available, preferably also serving as an energy source. An assimilable source of nitrogen is important and can be provided in a variety of ways known in the art. Phosphorus and potassium are necessary, as well as sulfur and trace elements. Various vitamins are need by certain yeasts under certain conditions. If the substrate proposed for growth of microorganisms lacks any of these factors, then nutrients must generally be added if the medium is to be useful.

An experiment was conducted to determine whether *C. utilis* required any vitamins in its growth medium. Table 1 shows that *C. utilis* does not need to be supplied with vitamins. The yeast is evidently able to synthesize its own vitamins.

In order to establish the ability of potato waste to support the growth of yeasts, the amounts of carbohydrate, nitrogen, and phosphate were determined. Carbohydrate is present in the potato waste as starch and glucose. Paper chromatography revealed that the only free sugar present in the medium was glucose. Maltose did not appear to be present in potato waste. Table 2 records the amounts of glucose, starch, nitrogen, and phosphate present in potato waste as milligrams of each per gram of waste. Nitrogen and phosphate appear to be present as constituents of organic molecules, as they could not be detected in potato waste without first subjecting it to digestion with sulfuric acid.

Figure 3:
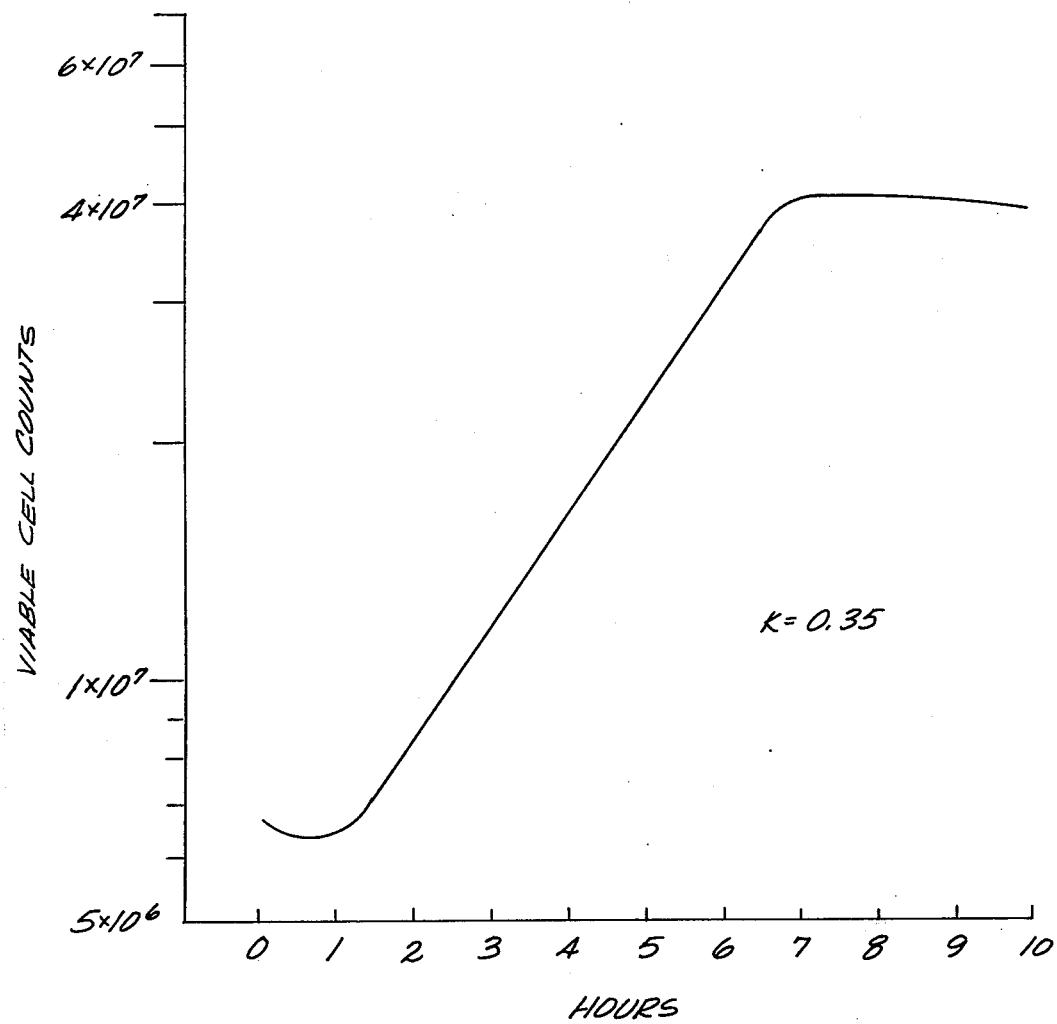
FIG. 3 is a graph illustrating the growth of *Candida utilis* on potato waste.

The growth of *C. utilis* in potato waste medium is shown in FIG. 3. Due to the extreme thickness of the medium, it was necessary to employ counts of viable cells as a measure of the growth of the yeast. The average doubling time of the yeast grown in potato waste medium at 25° C. in the gyrotory water bath shaker at 200 rotations per minute is 2.0 hours.

TABLE 1

| Determination of vitamin requirements for *Candida utilis* | | | | | |
|---|---|---|---|---|---|
| | Absorbance at 420nm after 72 hours growth in minimal medium[a] | | | | |
| Experiment No. | Biotin | Folic Acid | PABA[c] | Niacin | Pyridoxine |
| 1[b] | 0.06 | 0.07 | 0.06 | 0.06 | 0.04 |
| 2[b] | 0.1 | 0.1 | 0.09 | 0.1 | 0.08 |
| | Absorbance at 420nm after 72 hours growth in minimal medium[a] | | | | |
| Experiment No. | Pantothenate | Thiamine | Inositol | All | None |
| 1[b] | 0.10 | 0.07 | 0.06 | 0.09 | 0.09 |
| 2[b] | 0.09 | 0.09 | 0.09 | 0.07 | 0.08 |

[a]Experiment carried out at 25° C., pH 5.6, in still culture. All tubes were inoculated from a standard inoculum and contained too few cells to give an initial reading.
[b]These results represent the average of duplicate tubes.
[c]PABA = p-aminobenzoic acid.

TABLE 2

| | Composition of Potato Waste | | | |
|---|---|---|---|---|
| | mg/g wet weight | | | |
| | Glucose | Starch | Nitrogen | Phosphate |
| Exp. 1[a] | 21.0 | — | — | — |
| Exp. 2[a] | — | — | 6.5 | 0.90 |
| Exp. 3 | 20.0 | 19.2 | 5.9 | 0.72 |
| Exp. 4 | 20.0 | 20.0 | 6.1 | 0.84 |
| Exp. 5[a] | 22.0 | — | — | — |
| Exp. 6 | — | 22.0 | 6.1 | 0.76 |

[a]Certain components not tested for, hence no value is given

Figure 4:
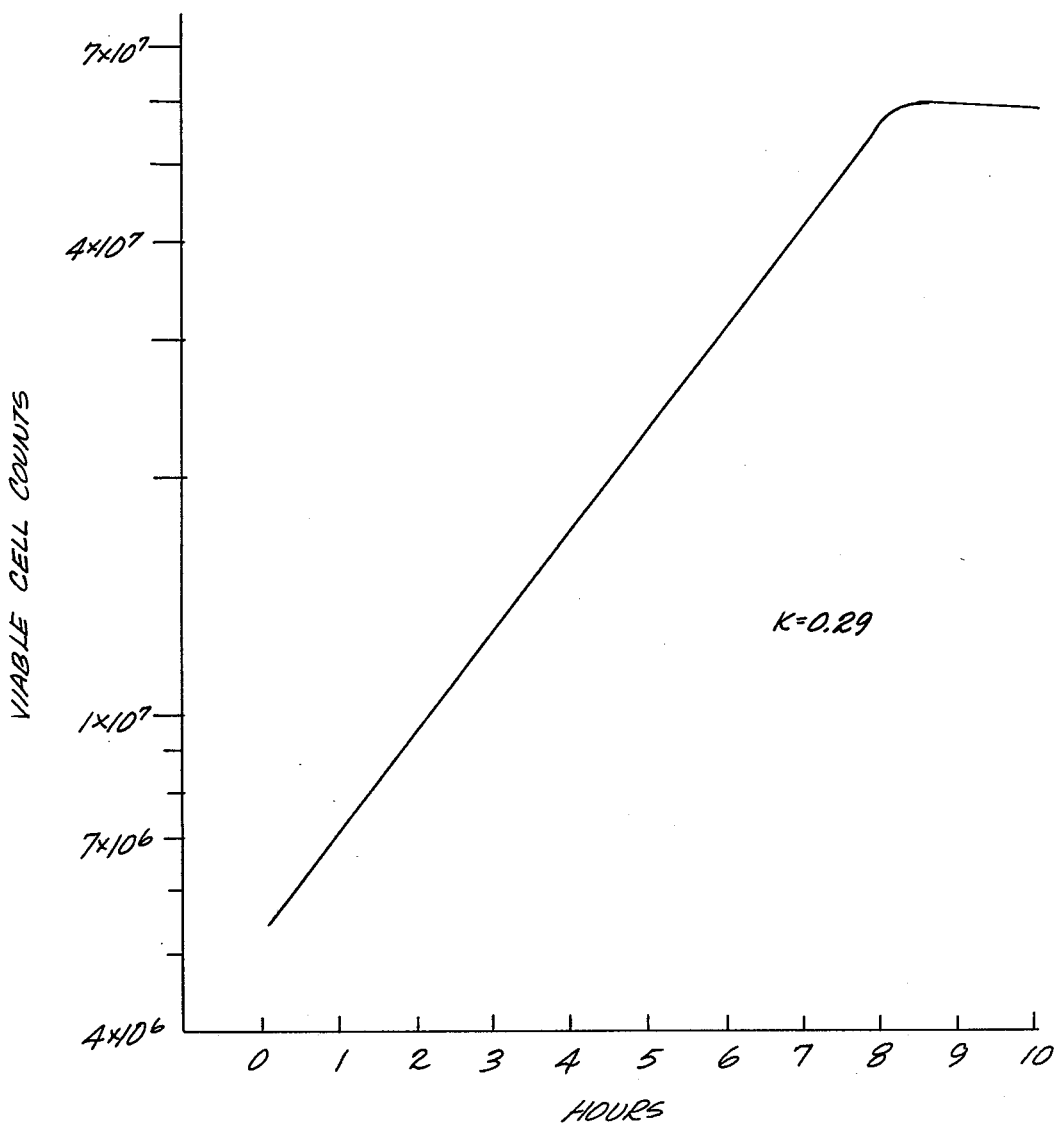
FIG. 4 is a graph illustrating the growth of *Candida utilis* on potato waste with 0.2% ammonium sulfate.
Figure 5:
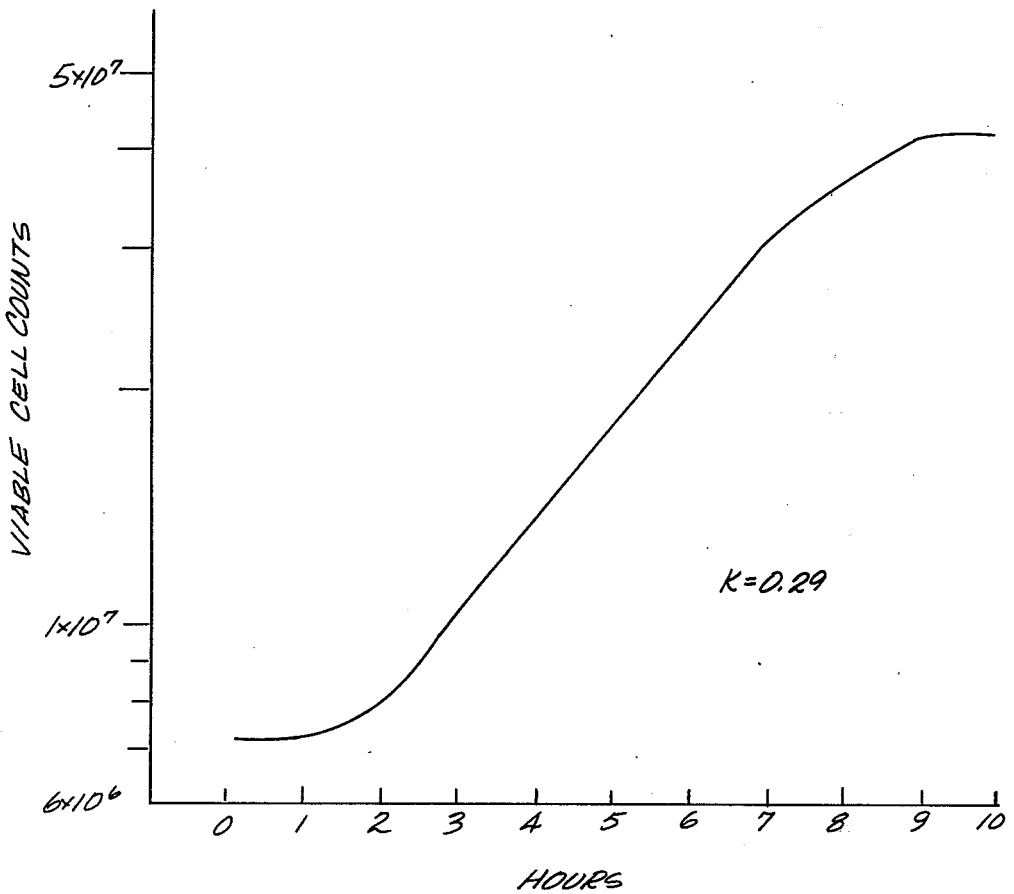
FIG. 5 is a graph illustrating the growth of *Candida utilis* on potato waste with 0.15% potassium dihydrogen phosphate.

Since the yeast ceased to grow in the potato waste long before all nutrients were used up, it was decided to determine whether some nutrient was limiting growth. The growth of *C. utilis* on potato waste medium with added $(NH_4)_2SO_4$ is shown in FIG. 4 and with added $KH_2PO_4$ in FIG. 5. The addition of these two inorganic salts did not seem to increase the growth rate or yield of the yeast. It was therefore assumed that the amounts of these factors in potato waste are not limiting the growth of *C. utilis*. The average doubling time of the yeast in the two media at 25° C. in the gyrotory water bath shaker at 200 rotations per minute was 2.4 hours.

Increased agitation and air flow have sometimes increased the yield of yeasts in various media. To determine whether the growth rate and yield of *C. utilis* could be increased in this manner, the yeast was grown in a New Brunswick batch fermentor on potato waste medium with added $(NH_4)_2SO_4$ at 25° C. with an agitation rate of 200 rpm and a filtered air flow rate of 10,000 cc per minute. It was demonstrated that increasing agitation and air flow did not increase the growth rate and yield of *C. utilis* on potato waste medium. The doubling time was 2.0 hours.

Figure 6:
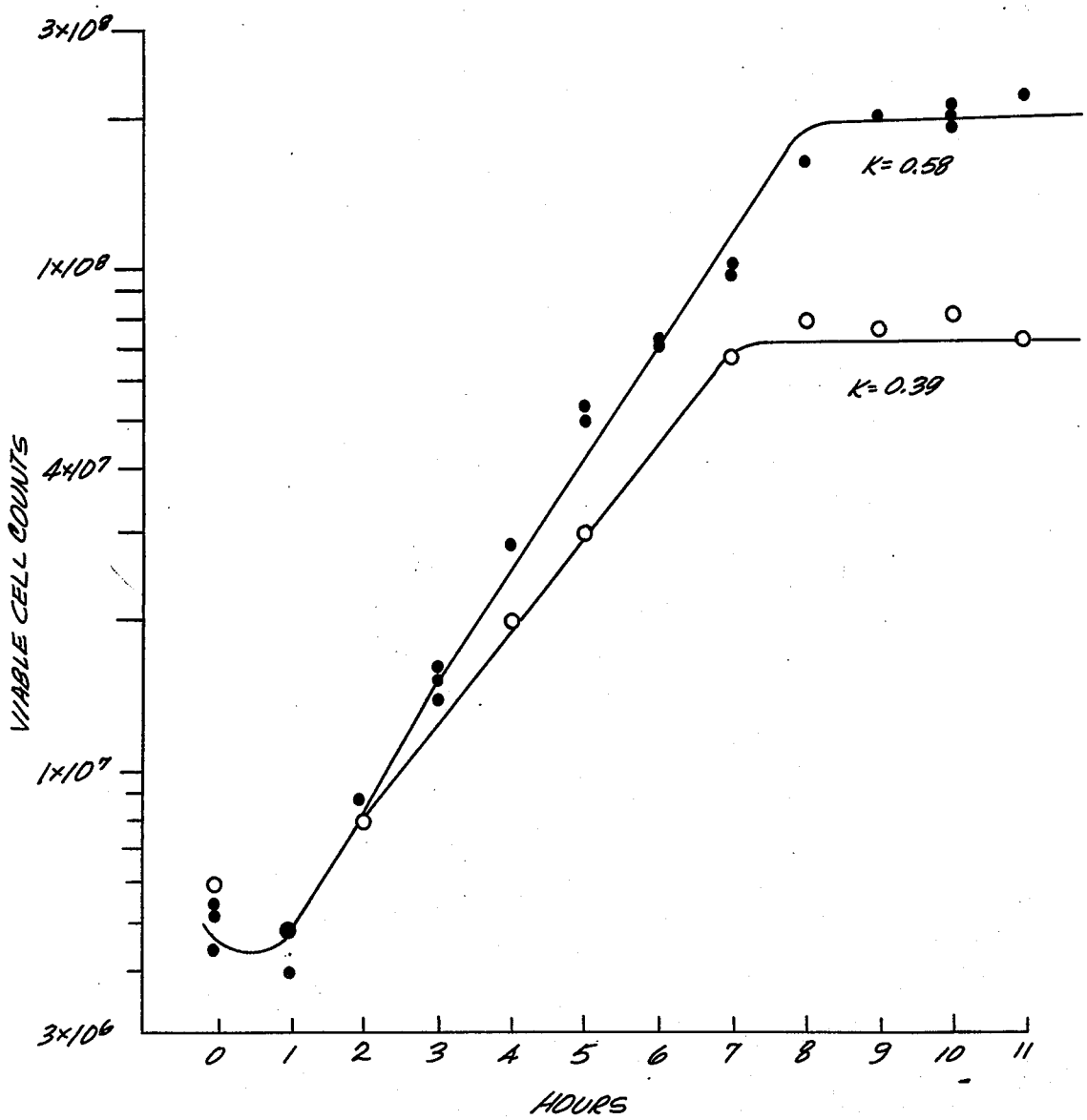
FIG. 6 is a graph illustrating the growth of *Candida utilis* and *Endomycopsis fibuliger* on potato waste.

It was also thought that the amount of free glucose might be limiting the growth of the yeast. Since most of the carbohydrate present in the potato waste medium is in the form of starch, it would need to be hydrolized in order to be made available to *C. utilis*. A method which has been used to hydrolize the starch is to grow *Endomycopsis fibuliger*, a yeast which produces external amylases, in mixed culture with *C. utilis*. Plate counts of viable cells were again used to monitor the growth of *C. utilis*, whose colonies are easily distinguishable from those of *E. fibuliger*. No representative growth rates for *E. fibuliger* could be obtained by using plate counts due to its pseudomycelial character. The result of the mixed culture is shown in FIG. 6. The open circles indicate growth of *C. utilis* alone in potato waste medium. It can be seen from the closed circles, which indicate the mixed culture, that the growth rate is increased, with a doubling time of 1.2 hours, and that the yield is increased by almost 3 times. The release of glucose from starch, and therefore its availability for use by *C. utilis*, is believed to be a factor responsible for these increases.

The data in Table 3 illustrate the carbohydrate concentration in potato waste medium during growth of the mixed yeast culture. Total carbohydrate, as expected, decreased during the course of the growth of the yeasts. The concentration of free glucose available for use by the yeasts increased and then decreased during the course of the experiment.

The growth rate constant k and mass doubling time of each of the various growth experiments are recorded in Table 4.

It should be noted that the fastest growth rate of *C. utilis* occured in mixed culture in potato waste medium.

TABLE 3

| Carbohydrate concentration in potato waste medium | | | | |
|---|---|---|---|---|
| | Glucose mg/ml | | Glucose and starch mg/ml | |
| Hour | Exp. 1 | Exp. 2 | Exp. 1 | Exp. 2 |
| 0 | 1.2 | 2.1 | 5.5 | 8.0 |
| 2 | 2.5 | 4.1 | — | — |
| 4 | 2.4 | 2.7 | 7.0 | 6.5 |
| 6 | 3.05 | 2.7 | — | — |
| 8 | 3.3 | — | 4.5 | 4.7 |
| 10 | — | 1.75 | — | — |
| 24 | 0.39 | — | 2.0 | — |

Certain yeasts exhibit the "Crabtree effect" when growing in the presence of glucose and air. That is, they degrade glucose mainly by aerobic fermentation with concomitant repression of respiratory pathways. To elicit this effect, the glucose concentration must usually be high, but it has been known to occur at concentrations of as little as 1 g/l. The effect of the glucose concentration on repression of the oxidative pathways predominates over the presence or absence of oxygen.

TABLE 4

Summary of growth rate constants of Candida utilis and Endomycopsis fibuliger under various conditions

| | Growth rate constant (k) | Mass doubling time (hrs) |
|---|---|---|
| C utilis on Sabouraud liquid medium[a] | 0.22 | 3.2 |
| E. fibuliger on Sabouraud liquid medium[a] | 0.27 | 2.6 |
| C. utilis on potato waste[b] | 0.35 | 2.0 |
| C. utilis on potato waste with 0.2% $(NH_4)_2SO_4$[b] | 0.29 | 2.4 |
| C. utilis on potato waste with 0.15% $KH_2PO_4$[b] | 0.29 | 2.4 |
| C. utilis on potato waste in fermentor[c] | 0.35 | 2.0 |
| C. utilis on mixed culture[b] | 0.58 | 1.2 |
| (C utilis alone as mixed culture control)[b] | (0.39) | (1.8) |

[a]Growth took place at 25° C., pH 5.7, in the New Brunswick gyrotory water bath at 100 rotations per minute.
[b]Growth took place at 25° C., pH 5.6, in the New Brunswick gyrotory water bath at 200 rotations per minute.
[c]Growth took place at 25° C., pH 5.6, in the New Brunswick laboratory 10 l fermentor, at 200 rpm and with a filtered air flow rate of 10,000 cc/min.

Growth of yeasts exhibiting the "Crabtree effect" is characterized by a glucose-ethanol diauxic growth curve. Two distinct phases are seen, the first being characterized by rapid growth during which the yeast ferments most of the glucose to ethanol. The second phase begins when the sugar in the medium is almost used up and is characterized by a slower rate of growth and a longer doubling time in which oxidative metabolism takes over from fermentative metabolism. Fermentation does not supply the yeast cell with the greatest amount of energy per glucose molecule utilized and so wastage of the glucose occurs in terms of cell energetics. The "Crabtree effect" would therefore be important to avoid in setting up a system to produce the maximum yield of yeast cells from the least amount of glucose.

Figure 7:
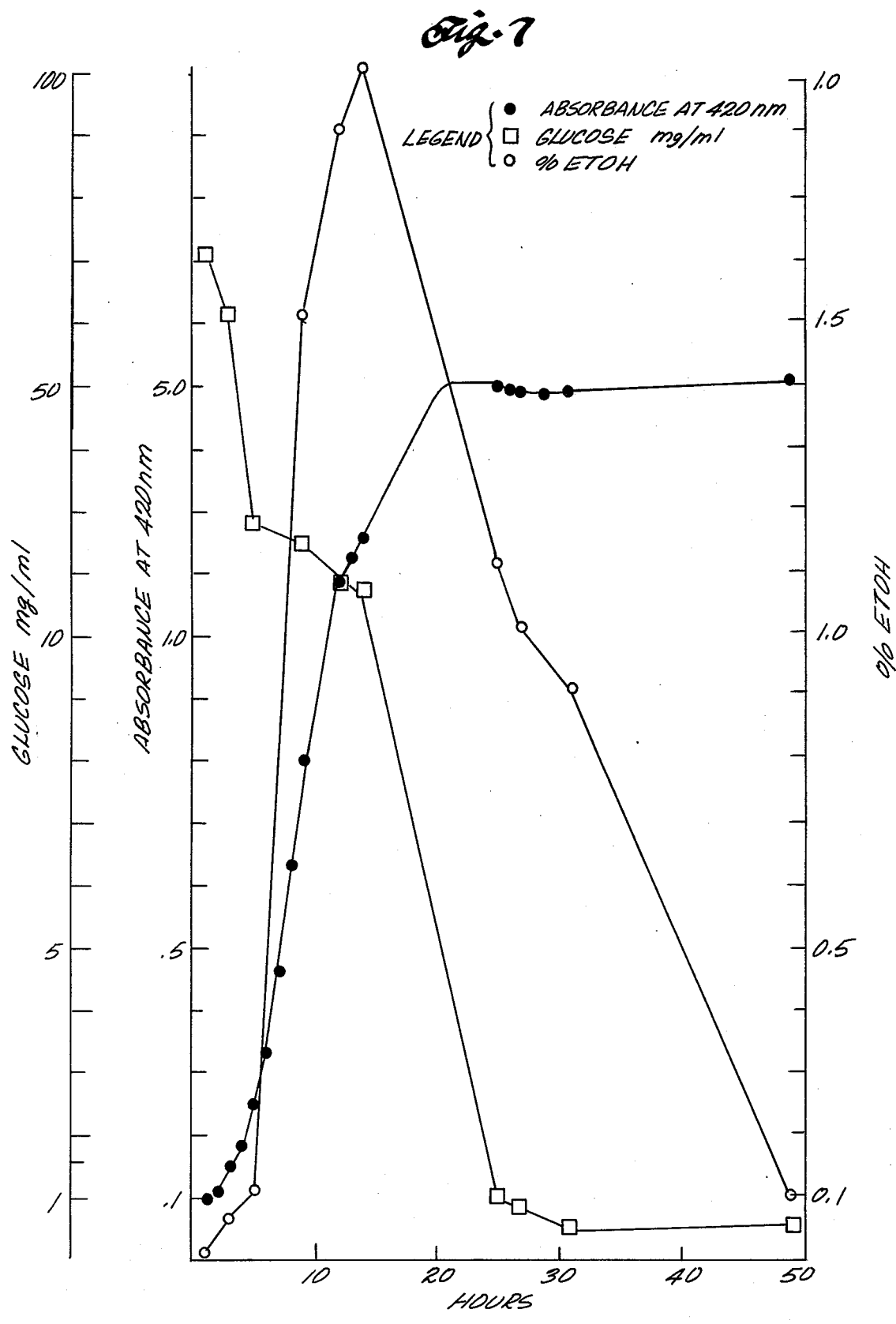
FIG. 7 is a graph illustrating the growth of *Candida utilis* on 7% glucose minimal medium.
Figure 8:
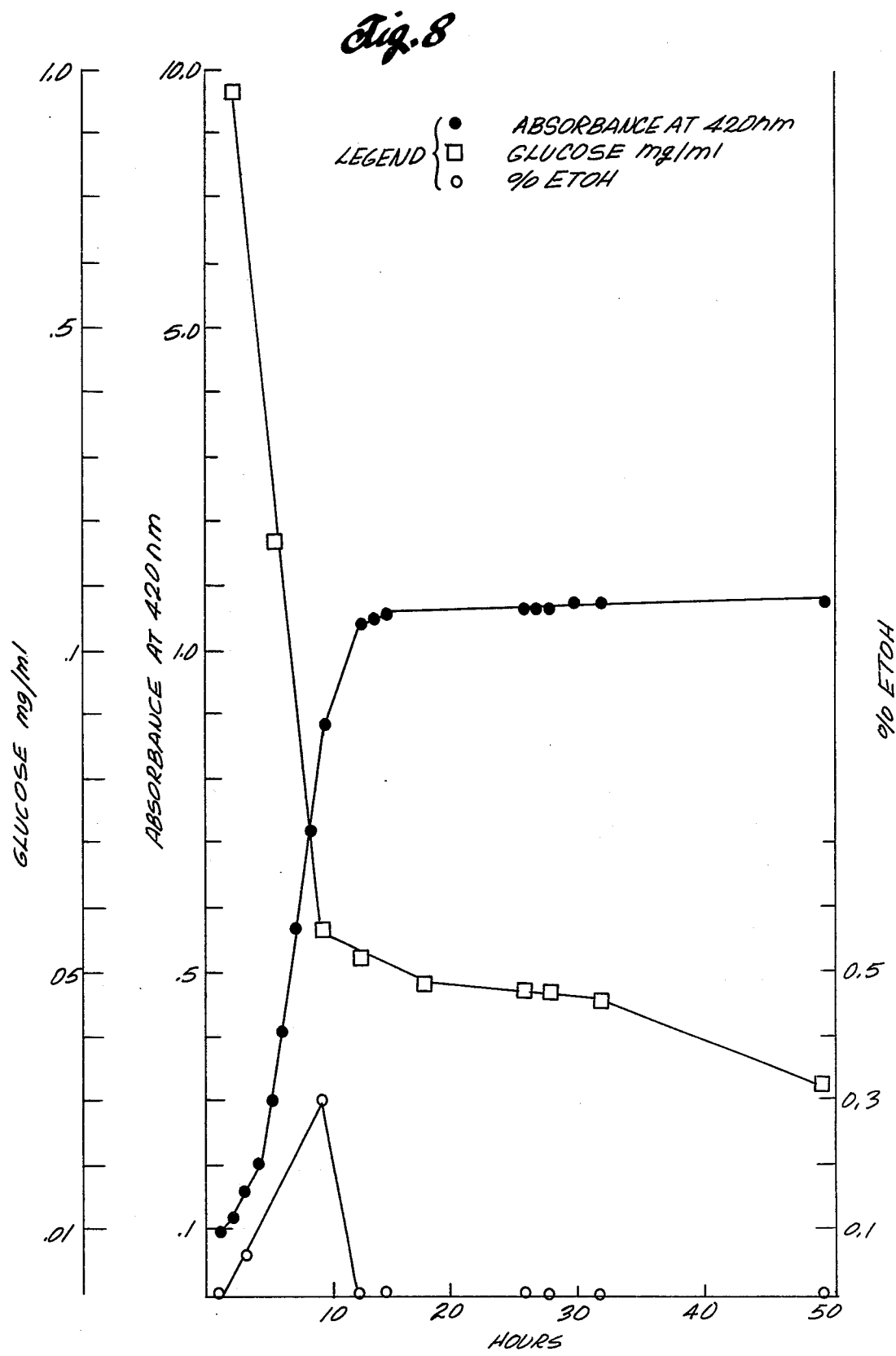
FIG. 8 is a graph illustrating the growth of *Candida utilis* on 0.1% glucose minimal medium.

The "Crabtree effect" has not been demonstrated in C. utilis. This yeast is an avid oxidizer of carbohydrates and when in log phase has been demonstrated to metabolize as much as 60-72% of assimilated glucose via the hexose monophosphate shunt. To test for the possible presence of the "Crabtree effect" in the C. utilis used in these studies, the yeast was grown in minimal medium with two concentrations of glucose, 7% and 0.1%. The results are shown in FIGS. 7 and 8 in which no "Crabtree effect" is noted. The doubling time in both cases was 2 hours with a growth rate value k of 0.35 per hour. The final density of cells as measured turbidimetrically was about 3 times as great in the case of the greater glucose concentration as in the lesser glucose concentration. However, it can be seen that in medium containing 7% glucose, approximately 70 times more sugar disappears than in medium containg 0.1% glucose. A periodate-schiff stain of the yeast cells from both situations revealed the presence of more intracellular polysaccharide in cells growing in the greater glucose concentration than in cells growing in the lesser concentration of glucose. This is an indication that the cells may be storing the glucose as glycogen, thereby preventing its use for energy-yielding metabolism.

It appears that this strain of C. utilis, when confronted with a high concentration of glucose, will do three things. First, some of the glucose will be metabolized via the hexose monophosphate shunt and TCA cycle to $CO_2$ and $H_2O$. Second, more of the pyruvate is converted to ethanol than in the lower concentration. Third, all cells will store a great amount of the glucose as glycogen.

Growing the yeast on a high concentration of glucose does not seem to be the most practical method of cultivating it, for it will remove many times the amount of glucose from the medium while only producing a few times the final cell density of a lesser glucose concentration medium. The growth rate in both cases remains identical, indicating that the cells are not stimulated to grow faster in the presence of greater concentrations of glucose. The greater glucose concentration does appear to be responsible for the slightly increased yield of cells in that it allows the cells the remain in log phase longer. These observations suggest that one should grow C. utilis on a medium containing a glucose concentration which would promote maximum growth rate and yield of cells, while causing them to utilize the glucose in the most efficient manner. They also suggest that the higher growth rate of C. utilis in mixed culture is due to something other than simply raising the concentration of available glucose in potato waste medium.

Tests were conducted to determine whether the yeast cells grown on potato waste would be able to augment the amounts of amino acids found in raw potato waste, thereby making the potato waste and yeast cell mixture a more nutritious food for animals. Table 5 shows the results of quantitative paper chromatographic amino acid studies of hydrolysates of raw potato waste and potato waste plus yeast cells grown on it. The presence of the yeast cells increased the amino acid content of potato waste approximately ten-fold. No single amino acid appeared to be increased over any other. The yeast decreased the carbohydrate concentration of potato waste, converting sugar to other cellular components including amino acids.

Thus it can be seen that it is possible to use potato waste filter cake as a growth medium for the cultivation of Candida utilis, which, in turn, becomes a source of single-cell protein. Such potato waste is an economic medium, in that no growth factors need be added to it to promote production of the yeast. Production of the yeast at 25° C. is also economical because it eliminates the need for expensive heating and cooling equipment which is necessary to regulate systems operating at higher or lower temperatures.

Table 5

Amino acid composition of potato waste before and after growth of yeast.

| | | μM/g wet weight | | | | | |
|---|---|---|---|---|---|---|---|
| | | leu, isoleu | phe | val, met | tyr tyrp | pro | ala |
| Potato waste | Exp. 1 | 3.5 | 1.3 | 3.2 | 0.67 | 0.33 | 2.8 |
| | Exp. 1 | 4.2 | 2.2 | 3.7 | 0.83 | 0.67 | 3.5 |
| Potato waste plus C. utilis and E. fibuliger cells | Exp. 1 | 35.0 | 10.0 | 37.0 | 12.0 | 8.0 | 40.0 |
| | Exp. 2 | 42.0 | 6.7 | 50.0 | 17.0 | 6.7 | 45.0 |

| | | μM/g wet weight | | | |
|---|---|---|---|---|---|
| | | thr | gly, ser | glu, glutam lys, arg, his | asp |
| Potato waste | Exp. 1 | 3.0 | 1.7 | 2.0 | 1.2 |
| | Exp. 2 | 3.0 | 2.7 | 1.8 | 1.7 |
| Potato waste plus C. utilis and E. fibuliger | Exp. 1 | 35.0 | 18.0 | 22.0 | 10.0 |

Table 5-continued

| | Amino acid composition of potato waste before and after growth of yeast. | | | | |
|---|---|---|---|---|---|
| cells | Exp. 2 | 45.0 | 23.0 | 27.0 | 8.3 |

The presence of *Endomycopsis fibuliger* in potato waste medium causes the conversion of starch to glucose, which then becomes utilizable by *C. utilis*. More utilizable glucose probably leads to increased yield of *C. utilis* by allowing it to stay in log phase longer. The presence of *E. fibuliger* also seems to promote a faster growth rate of *C. utilis* than is possible when growing that yeast alone. A continuous culture application appears to be possible, in that *E. fibuliger* could be allowed to release most or all of the glucose that is bound as starch in potato waste before *C. utilis* is introduced to the medium. The flow rate of the medium could then be regulated to allow the greatest growth rate and highest yield of *C. utilis* on an optimal concentration of glucose. High glucose concentrations lead to inefficient utilization of that carbon and energy source by *C. utilis*.

The amino acid composition of potato waste is increased while the carbohydrate content is decreased by the presence of yeast cells grown on it, making potato waste plus yeast cells a better animal feed than potato waste alone. It could also be practical to separate the yeast cells from the potato waste medium and use them as animal or human food supplements.

The method of this invention produced the following unexpected results.

(1) The yeast grew well in a high solids medium, a situation that often prevents growth of microbes due to unfavorable water activity and osmotic pressures. The yeast grew as well in a very high concentration of filter cake in water as they did in a low concentration of a filter cake in water. For example, the yeast grew in a potato waste medium containing more than 50% filter cake by weight (exclusive of the water content of the potatoes). This discovery could yield reduced operating costs in a commercial plant due to reduced usage of water as the dilution medium and reduced water pollution problems.

(2) No additional growth factors needed to be added to the filter cake to promote good growth of the yeast. This was surprising, inasmuch as the filter cake generally undergoes some quite drastic chemical treatments during processing of the potatoes. Not having to add growth factors reduces the cost of commercial operation and simplifies control of growth.

(3) The presence of too much glucose in the growth medium leads to inefficient conversion of glucose into cell mass. The presence of *E. fibuliger* is therefore necessary, not only for conversion of starch to glucose, but also to help keep the glucose at a good level for *C. utilis* growth.

(4) The filter cake medium can be used a relatively long period of time before its ability to promote yeast growth is exhausted. This is due to an unexpected amount of starch and nutrients contained in it. It therefore could produce more yeast on a weight basis than could liquid effluent growth medias.

(5) The yeasts produce a better yield of cells in the same growth period on the potato processing filter cake medium than they do in a laboratory medium designed specifically for cultivation of yeasts, which demonstrated the surprising superiority of the filter cake as a growth medium.

EXAMPLES

The following are examples of the materials and methods used in the growth studies described above.

Organisms

The organisms used in the growth study, namely, *Candida utilis*, ATCC 9950 (NRRL Y-900), and *Endomycopsis fibuliger*, ATCC 9947 (NRRL Y-1062), were obtained from the American Type Culture Collection, Rockville, Md.

Media and Growth Conditions

*Candida utilis* ATCC 9950 (NRRL Y-900) was grown in the following media on a New Brunswick Scientific Co., Inc. gyrotory water bath shaker, model G76, at 25° C.

Sabouraud Liquid Medium

The medium used for overnight cultures was Difco number B382, Sabouraud liquid medium, prepared as directed in the Difco Manual.

Minimal Medium

A chemically defined minimal medium was prepared according to the method of Burkholder et al., 1944, "Studies on Some Growth Factors of Yeasts", J. Bacteriol, 48:385–391, and contained per liter: D-glucose, 20.0 g; L-asparagine, 2.0 g; $KH_2PO_4$, 1.5 g; $MgSO_4.7H_2O$, 0.5 g; $CaCl_2.2 H_2O$, 0.33 g; $(NH_4)_2SO_4$, 2.0 g; KI, 0.1 g; and 1.0 ml of Nitsch's trace elements solution. Nitsch's trace element solution contained per 1 of distilled water: $H_2SO_4$, 0.5 ml; $MnSO_4.H_2O$, 2.2 g; $ZnSO_4.7 H_2O$, 0.5 g; $H_3BO_3$, 0.5 g; $CμSO_4$, 0.016 g; $Na_2MoO_4.2 H_2O$, 0.025g; and $CoCl_2.6 H_2O$, 0.046 g. The final pH of the solution was adjusted to 5.6 with 1.0 N KOH. The solution was sterilized in an autoclave for 15 minutes at 15 pounds pressure, 121° C.

Potato Waste Medium

A growth medium using potato waste was prepared. The waste was supplied as filter cake by the American Potato Co., Blackfoot, Idaho. The medium was prepared in 250 ml Erlenmeyer flasks by adding 10.0 g of raw filter cake to 25.0 ml of distilled water. The pH was adjusted to 5.6 with 1.0 N KOH, and the flasks were covered with aluminum foil and sterilized in an autoclave for 15 minutes at 15 pounds pressure, 121° C.

Potato Waste Medium with Added Nitrogen

A growth medium using potato waste was prepared by adding 10.0 g of filter cake to 25 ml of a 0.2% $(NH_4)_2SO_4$ solution. Conditions of preparation were the same as that described for the potato waste medium.

Potato Waste Medium with Added Phosphate

A growth medium using potato waste was prepared by adding 10.0 g of filter cake to 25 ml of a 0.1% $KH_2PO_4$ solution. Conditions of preparation were the same as that described for the potato waste medium.

Stock Cultures

Stock cultures of *C. utilis* were maintained on Sabouraud dextrose agar, Difco number B109, prepared as directed in the Difco Manual. The cultures were kept on agar slants in screw cap test tubes. The slants were inoculated with the organism using a sterile wire loop. Two stock culture slants were maintained at all times, a master slant and a working slant. The inoculated slants were allowed to incubate at 25° C. for two days in a Central Scientific Co. incubator, model 95105A. They were then stored at 5° C. for two weeks, at which time cells were then transferred to fresh slants. The old slants were sealed with parafilm and stored at 5° C.

Media Used with E. fibuliger

The Sabouraud liquid medium, the potato waste medium, and the stock culture medium were used to grow E. fibuliger. All media were prepared as previously described, and the stock cultures of E. fibuliger were maintained and stored as described for C. utilis.

Growth Experiments

Overnight Cultures

Overnight cultures were grown by inoculating 25 ml of Sabouraud liquid medium with cells from the working stock culture tube using a sterile wire loop. The medium was contained in cotton-stoppered 250 ml Erlenmeyer flasks, previously sterilized. Inoculated flasks were allowed to grow overnight in the gyrotory water bath shaker at 25° C., at 100 rotations per minute.

Growth in Sabouraud Liquid Medium

Growth experiments were carried out on C. utilis and E. fibuliger in foil-covered 1 liter Erlenmeyer flasks containing 100 ml of Sabouraud liquid medium. The flasks were placed in the gyrotory water bath shaker at 25° C. and were shaken at 100 rotations per minute. Separate flasks were inoculated with 15 ml of an overnight culture of either C. utilis or E. fibuliger and hourly readings of absorbance at 420 nm were taken to measure increases in turbidity for each organism until stationary growth was achieved using a Coleman linear absorbance spectrophotometer, model 44. These experiments were done to determine growth rates and the length of time the organisms were in their exponential phase of growth. The growth rate constant, k, was determined for logarithmically growing cultures using the relationship:

$$k = \frac{\ln 2}{\text{mass doubling time in hours}}$$

Growth in Potato Waste

Growth experiments were carried out on C. utilis in the prepared 250 ml Erlenmeyer flasks containing potato waste medium. Three ml of an overnight culture of C. utilis were added to each flask, and the flask placed in the gyrotory water bath at 25° C. and at 200 rotations per minute. As soon as the 3 ml of overnight culture were added, plates of Sabouraud dextrose agar medium were inoculated in order to obtain counts of viable cells. Plates were inoculated every hour thereafter until stationary growth was achieved to obtain a measure of the growth rate of the organism using counts of viable cells.

Dilutions prior to plating were made by taking 0.1 ml of the inoculated growth medium and placing it in a 9.9 ml sterile distilled water blank. Successive dilutions were made in sterile distilled water blanks. The inoculated plates were spread with a glass hockey stick spreader sterilized in flaming alcohol. Incubation of the plates took place for 2 days in the Central Scientific Co. incubator at 25° C. Colonies were counted in an automatic colony counter, and the average of two plates inoculated at the same time was recorded.

The growth rate constant, k, was determined for logarithmically growing cultures as described above.

Growth in Potato Waste with Added Nitrogen

Growth experiments were carried out on C. utilis in the prepared 250 ml Erlenmeyer flasks containing potato waste medium in 0.2% $(NH_4)_2SO_4$ solution. All conditions and procedures were the same as in the potato waste medium growth experiment.

Growth in Potato Waste with Added Phosphate

Growth experiments were carried out on C. utilis in the prepared 250 ml Erlenmeyer flask containing potato waste medium in 0.15% $KH_2PO_4$ solution. All conditions and procedures were the same as in the potato waste medium growth experiments.

Growth in Batch Fermenter

A growth experiment was carried out using C. utilis in a Microferm laboratory fermentor, New Brunswick Scientific Co., Inc., model MF-14. Twelve hundred grams of filter cake were added to 3000 ml of a 0.2% $(NH_4)_2SO_4$ solution in the fermentor jar and sterilized in an autoclave for 45 minutes at 15 pounds pressure, 121° C. The fermentor was inoculated with 360 ml of overnight culture, and plate counts were made initially and every hour thereafter using the same conditions and with the same procedures as the potato waste medium growth experiements. The agitation rate of the fermentor was 200 rpm, the temperature was maintained at 25° C., and the sterile air flow rate was 10,000 cc/minute.

Growth of C. utilis and E. fibuliger in Mixed Culture

Growth experiments on C. utilis and E. fibuliger were carried out by growing both organisms simultaneously in prepared flasks of potato waste medium in distilled water. Three ml of each overnight culture of the two organisms were added at the same time to one flask of the growth medium. Plate counts were made initially and every hour thereafter as described above.

Colonies of C. utilis were counted and recorded, giving only an indication of C. utilis growth in the mixed culture. Due to its mycelial character, E. fibuliger did not give plate counts representative of its growth. Colonies of C. utilis were moist, circular, entire, opaque, convex, and had a beige tint. They were easily distinguishable from colonies E. fibuliger which were filamentous, circular, and had an off-white color.

Growth in Minimal Medium

Growth experiments were carried out on C. utilis in foil covered 1 liter Erlenmeyer flasks containing 100 ml of minimal medium. Two concentrations of glucose were used, 0.1% and 7%. Separate flasks of each concentration were inoculated with 15 ml of an overnight culture of C. utilis and hourly readings of absorbance at 420 nm were taken until stationary growth was achieved using a Coleman linear absorbance spectrophotometer, model 44. In addition, 3 ml of each flask were removed at regular intervals to determine ethanol production and glucose utilization. Growth rate constant, k, was calculated as previously described.

Vitamin Requirements

An experiment to determine any vitamin requirements for *C. utilis* was done according to the method of Burkholder et al., supra. Vitamin starved cells were prepared in 100 ml of minimal medium in a cotton stoppered 1 liter Erlenmeyer flask by inoculating the medium with cells from the working stock culture tube using a sterile wire loop. The culture was allowed to grow for 48 hours at 25° C. in the gyrotory water bath shaker at 100 rotations per minute.

The following vitamins were assayed in the indicated concentrations: biotin, 0.002 $\mu$g per ml; folic acid, 0.002 $\mu$g per ml; para-aminobenzoic acid, 0.2 $\mu$g per ml; nicotinic acid, 0.4 $\mu$g per ml; pyridoxine HCl, 0.4 $\mu$g per ml; DL-calcium pantothenate, 0.4 $\mu$g per ml, thiamine HCl, 0.4 $\mu$g per ml; and inosital, 2.0 $\mu$g per ml. Test tubes containing 5 ml of minimal medium and all but one of each vitamin were prepared in duplicate; and 16 tubes in all were prepared in this manner for each experiment. In addition, 2 tubes containing no viamins and 2 tubes containing all the vitamins were prepared for each experiment. The test tubes were sterilized in an autoclave for 15 minutes at 15 pounds of pressure, 121° C., and the filter sterilized minimal medium containing the vitamins was added to the sterilized test tubes.

A yeast inoculum was prepared by transferring 0.01 ml of the vitamin-starved yeast culture to 5 ml of vitamin free minimal medium. Each assay tube was inoculated with 0.01 ml of this inoculum. The cells were allowed to grow for 72 hours in still culture in the Central Scientific Co. incubator at 25° C. After 72 hours, growth was measured turbidimetrically on the Beckman spectrophotometer, model 44, at 420 nm. The absorbance readings of duplicate tubes were averaged. The entire experiment was done twice.

Analyses on Potato Waste

Digestion of Samples for Analysis

Samples of raw potato waste were digest prior to analysis according to the method of Johnson, 1941, "Isolation and Properties of a Pure Yeast Polypeptidase," *J. Biol. Chem*, 137: 575-586. The samples were placed in 18 × 150 mm Pyrex test tubes and 1 ml of 2 N $H_2SO_4$ containing 0.2 g per liter of $CuSeO_3$ was added to cover the sample. The tubes were covered with small glass beakers and placed in a digestion rack. They were heated at 300° C. for 18 hours. A faintly brown liquid residue remained at the end of the digestion, and analysis was done on this residue.

Total Nitrogen Assay

Potato waste was assayed colorimetrically for total nitrogen by the method of Johnson, supra. Samples of filter cake weighing 0.01 g were digested according to the previous method. After digestion the residue was diluted by adding 4 ml of distilled water. To 2 ml of this dilution were added in order: 2 ml of color reagent and 3 ml of 2 N NaOH. The color reagent contained per liter: KI, 4 g; $HgI_2$, 4 g; and gum ghatti, 1.75 g. The gum ghatti was finely powdered, dropped in 750 ml of boiling distilled water, and refluxed until dissolved, a process of about 18 hours duration. The KI and $HgI_2$ were dissolved in 25 ml distilled water, and this was added to the gum ghatti solution. The entire mixture was made to 1 liter with distilled water and the color reagent was ready for use.

When all reactions had been added to the tube, it was allowed to stand 15 minutes while color developed. Absorbance was measured in a Beckman spectrophotometer, model 44, at 490 nm. A blank and nitrogen standards were developed with each sample.

A standard ammonium sulfate solution was made by dissolving 9.433 g of anhydrous $(NH_4)_2SO_4$ in 1 liter of N/5 sulfuric acid. This solution contained 0.20 mg of nitrogen per ml. 20 ml of it were pipetted into a 1 liter volumentric flask, 180 ml of N/5 sulfuric acid were added, and distilled water was added to make 1 liter of solution. This solution contained 0.040 mg of nitrogen per ml. The method is sensitive to a concentration of 1–40 $\mu$g of nitrogen.

Organic Phosphate Assay

Potato waste was assayed colorimetrically for total organic phosphate by a modification of the method of Fiske and Subbarow, 1925, "The Colorimetric Determination of Phosphorus," *J. Biol. Chem.*, 66: 375-400. Samples of filter cake weighing 0.1 gram were digested according to the previous method. After digestion the residue was diluted by a factor of 1:2 with distilled water. To an aliquot of this dilution were added, in order: 3 ml of distilled water, 1 ml of acid molybdate reagent, 1 ml of reducing reagent, and 5 ml of distilled water. To make the acid molybdate reagent, 25 g $(NH_4)_6Mo_7O_{24}.4\ H_2O$ were dissolved in 500 ml distilled water. This solution was added to 272 ml of 50% sulfuric acid. The entire mixture was made up to 1 liter with distilled water. To make the reducing reagent, 3 g $NaHSO_3$ and 1 g paramethylaminophenol were distilled in 100 ml distilled water.

When all reactants had been added to the tube, it was allowed to stand for 20 minutes while color developed. Absorbance was measured in a Beckman spectrophotometer, model 44, at 660 nm. The method produces a linear curve in a concentration range of 0.1–1.0$\mu$ mole of phosphate. A blank and phosphate standards were developed with each sample.

A standard phosphate solution was made to be 1$\mu$ mole per ml by dissolving 136 mg $KH_2PO_4$ in 1 liter of distilled water.

Total Carbohydrate Assay

Potato waste was assayed colorimetrically for total carbohydrate content by modifications of the anthrone method of Seifter et al., 1950, "The Estimation of Glycogen with the Anthrone Reagent", *Archives of Biochem*, 25: 191-200. Three assays were performed. In each, the anthrone reagent was made by dissolving 0.2 gram of anthrone in 100 ml of concentrated sulfuric acid. Absorbance was measured in a Beckman spectrophotometer, model 44, at 620 nm.

The first assay was done to find total carbohydrate content of 1 g of potato waste. One gram of filter cake was suspended in 3 ml of 30 KOH in a 16 by 150 mm test tube and the tube heated for 20 minutes in a boiling water bath. The tube was cooled in an ice bath and the contents diluted to 50 ml with distilled water. Serial dilutions were then made in distilled water. One ml of each dilution was placed in a 16 by 150 mm test tube and 2 ml of anthrone reagent was added and mixed immediately. The tube was capped with a marble, heated for ten minutes in a boiling water bath, and cooled in ice water. An absorbance reading in the spectrophotometer was then taken and recorded for those tubes that had readings in the range of the standard curve.

The second assay was done to find total carbohydrate content of the potato waste medium while *C. utilis* and *E. fibuliger* were growing on it. One ml samples of the medium were taken at regular intervals during growth of the organisms and were subjected to the same treatment as the filter cake in the first total carbohydrate assay.

The third assay was done to measure the disappearance of glucose from minimal medium during growth of *C. utilis*. Three ml samples of the minimal medium were taken at regular intervals and the cells allowed to settle. One ml of each sample was serially diluted in distilled water. Two ml of anthrone reagent were added to 1 ml of each of these dilutions in a 16 by 150 mm test tube and mixed immediately. The tubes were capped with marbles, heated for 10 minutes in a boiling water bath, and cooled in ice water. A reading of absorbance was taken and recorded for those tubes that had readings in the range of the standard curve.

A blank and glucose standards were developed with each assay. The method gives linear results from 0–100 $\mu$g glucose. The standard glucose solution contained 100 $\mu$g of glucose per ml.

Assay of Reducing Sugar in Potato Waste Medium

Potato waste medium was assayed colorimetrically for reducing sugar content during the growth of C. utilis and E. fibuliger by a modification of the method of Flood and Priestly, 1973, "Two Improved Methods for the Determination of Soluble Carbohydrates", J. Sci. Fd. Agric., 24: 945-955. Two ml samples of potato waste medium were collected at regular intervals and centrifuged at 8,000 rpm for 15 minutes in a Sorvall refrigerated centrifuge, model RC2-B. The supernatants, containing reducing sugar, were collected and 1 ml of each was serially diluted in distilled water. One ml of each dilution was pipetted into 16 by 150 mm test tubes. One ml of buffered ferricyanide solution was added to each tube, and the tubes were heated in a boiling water bath for 15 minutes. They were cooled, and 1 ml of arsenomolybdate reagent was added to each tube. After 5 minutes, 7 ml of distilled water was added, and the tubes were allowed to stand for one hour. Absorbance was measured in a Beckman spectrophotometer, model 44, at 740 nm.

The buffer contained per liter: $K_2HPO_4$, 140 grams and $K_3PO_4$, 42 grams. The potassium ferricyanide solution contained 16.5 g $K_3Fe(CN)_6$ per liter. The buffered ferricyanide solution was made by fixing 10 ml of the potassium ferricyanide solution with 50 ml of the buffer and making up the mixture to 100 ml with distilled water. The arsenomylybdate reagent was made by dissolving 25 grams $(NH_4)_6Mo_7O_{24}.4 H_2O$ in 450 ml distilled water and adding 21 ml of concentrated sulfuric acid to the solution. Three grams $Na_2HAsO_4.7 H_2O$ were dissolved in 25 ml distilled water and added to the acid molybdate solution. The reagent must be stored in a brown bottle for 24 hours at 37° C. before use.

A blank and glucose standards were developed with each assay. The method gives a linear curve from 0–40 $\mu$g of glucose, and the standard glucose solution was made to contain 40 $\mu$g of glucose per ml.

Determination of Starch in Potato Waste

Potato waste was assayed colorimetrically for starch content using the method of McReady et al., 1950, "Determination of Starch and Amylose in Vegetables", Anal. Chem., 22:1156–1162. A blank and glucose standards were developed with each assay. The method gives a linear curve from 0–100 $\mu$g of glucose, and the standard solution was made to contain 100 $\mu$g of glucose per ml.

Chemicals

All amino acids, sugars, and vitamins were obtaine from Sigma Chemical Company. All of the amino acids used were L isomers. All other chemicals used, unless stated otherwise, were commercial products of the highest grade available.

Thus, it has been demonstrated that potato processing wastes can be used as a substrate for supporting growth of single-cell protein. Once the filter cake has been used as the growth medium it can be dried along with the yeast as part of a complete animal feed, or it can be separated from the yeast by centrifuging or filtration and recycled for more use as a growth substrate until it virtually disappears, or is reduced to cellulositic components which can be burned to generate steam, or put to some other practical use. In addition, the water used to suspend the solid waste will have retained some starch and can be recycled for more yeast growth until the B.O.D. is reduced to acceptable levels. The water then can be recycled for other clean uses. Moreover, using the filter cake eliminates the necessity of adding growth factors or nutrients for the yeast, which provides a cost saving.

I claim:

1. A method for producing single-cell protein comprising the steps of:
   providing as a growth medium consisting essentially of an aqueous suspension of a filter cake waste product of potato processing, said filter cake consisting essentially of a semi-solid gel-like mass of particulate potato material and peels removed by a screening process in a potato processing plant;
   preparing a fermentation mixture consisting essentially of said growth medium, a pre-fermenting yeast capable of producing amylase for breaking down starch in the growth medium to glucose, and a primary fermenting yeast capable of utilizing such glucose to support its growth; and
   growing both the pre-fermenting yeast and the primary fermenting yeast in said fermentation mixture.

2. The method according to claim 1 including the step of pre-digesting the growth medium by initially introducing the pre-fermenting yeast into the growth medium to initiate the step of breaking down starch present in the medium to glucose, followed by introducing the primary fermenting yeast to the pre-digested growth medium.

3. The method according to claim 2 in which the pre-fermenting yeast is *Endomycopsis fibuliger*.

4. The method according to claim 3 in which the primary fermenting yeast is *Candida Utilis*.

5. The method according to claim 1 in which the growth medium contains about 4% glucose and starch, about 7% nitrogen and less than about 1% phosphate before preparation of the fermentation mixture.

6. A method for producing a single-cell protein comprising the steps of:
   providing as a growth medium consisting essentially of an aqueous suspension of a filter cake waste product of potato processing, said filter cake consisting essentially of a semi-solid gel-like mass of particulate potato material and peels removed by a screening process in a potato processing plant;

introducing into said growth medium a pre-fermenting yeast capable of producing amylase for breaking down starch in the growth medium to glucose;

introducing into said growth medium a primary fermenting yeast capable of utilizing such glucose to support its growth; and growing the pre-fermenting yeast and the primary fermenting yeast in the growth medium essentially in the absence of extraneously added vitamins, protein, glucose, nitrogen or phosphate.

7. The method according to claim 6 including the step of pre-digesting the growth medium by initially introducing the pre-fermenting yeast into the growth medium to initiate the step of breaking down the starch present in the medium to glucose, followed by introducing the primary fermenting yeast to the pre-digested growth medium.

8. The method according to claim 7 in which the pre-fermenting yeast is *Endomycopsis fibuliger*.

9. The method according to claim 8 in which the primary fermenting yeast is *Candida utilis*.

10. The method according to claim 6 in which the growth medium contains about 4% glucose and starch, about 7% nitrogen and less than about 1% phosphate before the yeasts are introduced into it.

11. A method for producing a single-cell protein comprising the steps of:

providing a growth medium consisting essentially of an aqueous suspension of a filter cake waste product of potato processing, said filter cake consisting essentially of a semi-solid gel-like mass of particulate material and peels containing about 4% glucose and starch, about 7% nitrogen and less than about 1% phosphate;

introducing into said growth medium a pre-fermenting yeast capable of producing amylase for breaking down starch in the growth medium to glucose;

introducing into said growth medium a primary fermenting yeast capable of utilizing such glucose to support its growth; and ;p1 growing the pre-fermenting yeast and the primary fermenting yeast in the growth medium essentially in the absence of extraneously added vitamins, protein, glucose, nitrogen or phosphate.

12. The method according to claim 11 in which the pre-fermenting yeast is *Endomycopsis fibuliger*.

13. The method according to claim 12 in which the primary yeast is *Candida utilis*.

* * * * *